United States Patent
Ginggen et al.

(10) Patent No.: US 6,600,945 B2
(45) Date of Patent: *Jul. 29, 2003

(54) IMPLANTABLE NUCLEAR MAGNETIC RESONANCE SPECTROMETER

(75) Inventors: Alec Ginggen, Muntschemier (CH); Yanik Tardy, Geneveys/Coffrane (CH)

(73) Assignee: Medos S.A. (CH)

( * ) Notice: Subject to any disclaimer, the term of this patent is extended or adjusted under 35 U.S.C. 154(b) by 70 days.

This patent is subject to a terminal disclaimer.

(21) Appl. No.: 09/797,818

(22) Filed: Mar. 2, 2001

(65) Prior Publication Data

US 2001/0029331 A1 Oct. 11, 2001

(51) Int. Cl.[7] .............................. A61B 5/05; A61B 6/00

(52) U.S. Cl. ..................... 600/419; 600/415; 600/431; 324/308; 324/312

(58) Field of Search .................. 600/109, 413, 600/415, 419, 421, 422, 431, 411, 459, 521; 604/175; 436/173; 424/9.3, 9.37, 9.32; 324/306, 308, 309, 312, 321, 322, 201, 204

(56) References Cited

U.S. PATENT DOCUMENTS

| | | | | |
|---|---|---|---|---|
| 5,016,637 A | * | 5/1991 | Koizumi et al. | 324/306 |
| 5,035,231 A | * | 7/1991 | Kubokawa et al. | 600/411 |
| 5,072,732 A | * | 12/1991 | Rapoport et al. | 600/421 |
| 5,314,450 A | | 5/1994 | Thompson | |

FOREIGN PATENT DOCUMENTS

EP 377695 B1 11/1989

* cited by examiner

Primary Examiner—Tu Ba Hoang
(74) Attorney, Agent, or Firm—Eugene L. Szczecina, Jr.

(57) ABSTRACT

An implantable nuclear magnetic resonance spectrometer for measuring the chemical composition of a fluid or for measuring the flow rate of the fluid. The spectrometer includes a housing and a catheter traversing across the housing so that a fluid external to the housing may flow through the catheter within the housing. A permanent magnet is disposed within the housing and generates an intense homogenous magnetic field in the vicinity of the catheter. An electronic circuit is disposed within the housing for detecting and formatting a nuclear magnetic resonance excitation signal. An excitation coil is connected to the electronic circuit and is disposed about the catheter to expose the fluid within the catheter to the excitation signal and to collect the nuclear magnetic resonance excitation signal.

9 Claims, 1 Drawing Sheet

IMPLANTABLE NUCLEAR MAGNETIC RESONANCE SPECTROMETER

BACKGROUND

The present invention relates to a medical implant, more particularly to a medical implantable device comprising a magnetic nuclear resonance spectrometer arrangement capable of characterising and monitoring the local flow rate of a physiological fluid as well as its chemical composition.

Nuclear magnetic resonance is based on the following known principle. All atomic nuclei with an odd atomic mass or an odd atomic number (like hydrogen for example) possess an intrinsic nuclear magnetic momentum. Without entering the details, one can consider that this momentum is generated by the rotation of the proton around the nucleus. When a NMR active nucleus is placed in a static magnetic field, this momentum can take two different orientations. The momentum may take either an orientation parallel to the magnetic field or an antiparallel orientation relative to the magnetic filed. Considering a population of hydrogen atoms immersed in the same static magnetic field, the number of atoms having a parallel orientation is slightly greater than the number of atoms having an antiparallel orientation. This is due the fact that the parallel orientation is energetically more favourable. The passage from the parallel state to the anti parallel state occurs when the atoms absorb electromagnetic energy at a given frequency called the resonance frequency. This resonance frequency depends on the nucleus of the atom and on the intensity of the static magnetic field. A magnetic nuclear resonance apparatus works by analysing the signal emitted during the transition from the excited state (anti-parallel) to the state of equilibrium (parallel). The nuclei are placed in a high intensity static magnetic field and then exited with an electromagnetic wave having a frequency corresponding to the resonance frequency. When the return to the equilibrium state occurs, a signal having the same frequency as the excitation signal (resonance) is generated and can be measured thanks to an antenna.

The resonance detection may occur either at the stage of excitation, by measuring the energy absorption by scanning a range of frequency or when the atoms return to the state of equilibrium. In the later, one measures the electromagnetic signal emitted by the magnetic momentum returning to their equilibrium position. If other atoms than hydrogen atoms are present in the solution to be characterised, the spin of their electrons will generate a magnetic field at the microscopic level. Thus the hydrogen atoms are submitted to the static magnetic field generated by the NMR device to which is superposed locally the magnetic field generated by the electrons. This will alter the resonance frequency with a signature specific to the environment of the hydrogen atoms within the solution to characterise. Nuclear magnetic resonance spectroscopy is based on this principle and is mainly used for two different kind of applications, namely for biochemical analysis in laboratories and in magnetic resonance imaging spectroscopy. In laboratories, nuclear magnetic resonance spectroscopy is usually performed at very high magnetic field intensity (>10 Tesla) to reveal the atomic structure of molecules. In contrast magnetic resonance imaging spectroscopy (MRIS) is performed with standard MRI equipment at lower filed intensity (around 1.5 Tesla) to reveal the composition of the tissues environment at molecular level.

It is also possible to gather information related to the flow of a liquid by analysing the signal returning to the equilibrium state after a resonant excitation. This signal has a decrease, which is characteristic when the liquid is static, and a faster decrease when the liquid is in movement. This is due to the fact that part of the excited atoms will leave the detection volume of the antenna. This technique also used in magnetic resonance imaging spectroscopy devices.

Chronic monitoring of specific chemical compounds in a body fluid as well as gathering information relative to the flow rate of a fluid within the human body is a key in many areas of medicine, this is particularly true for brain metabolites monitoring in trauma patient or for monitoring the flow rate of the cerebrospinal fluid in a shunted hydrocephalic patient. The known techniques for monitoring the concentration of specific chemical compounds in a physiological fluid are usually achieved invasively either by techniques that require taking samples of the fluid (dialysis, . . . ) or by inserting probes in the targeted fluid/tissue (micro dialysis, blood gas analysis.) These techniques involve either a puncture for each sample to analyse or a catheter line to be left in place for the duration of the monitoring. Furthermore, invasive catheter probes are mainly targeted to specific analytes such as $O_2$, $CO_2$, glucose or lactose.

Other non-invasive techniques such as magnetic resonance imaging spectroscopy are rather expensive and do not permit a continuous monitoring. Moreover, concerning the flow rate assessment, there are currently no known devices to perform these measures in situ.

SUMMARY OF THE INVENTION

The aim of the present invention is to remedy the aforesaid drawbacks. This goal is achieved by an implantable nuclear magnetic resonance spectrometer for measuring the chemical composition of a fluid or for measuring the flow rate of the fluid. The spectrometer includes a housing and a catheter traversing across the housing so that a fluid external to the housing may flow through the catheter within the housing. A permanent magnet is disposed within the housing and generates an intense homogenous magnetic field in the vicinity of the catheter. An electronic circuit is disposed within the housing for detecting and formatting a nuclear magnetic resonance excitation signal. An excitation coil is connected to the electronic circuit and is disposed about the catheter to expose the fluid within the catheter to the excitation signal and to collect the nuclear magnetic resonance excitation signal.

Yet another objet of the invention is the use of said implantable nuclear resonance spectrometer in several medical applications.

Further features and other objects and advantages of this invention will become clear from the following detailed description made with reference to the accompanying drawings illustrating in a schematic and non-limiting way one embodiment of the implantable nuclear magnetic resonance spectrometer.

DETAIL OF DESCRIPTION

Figure 1:
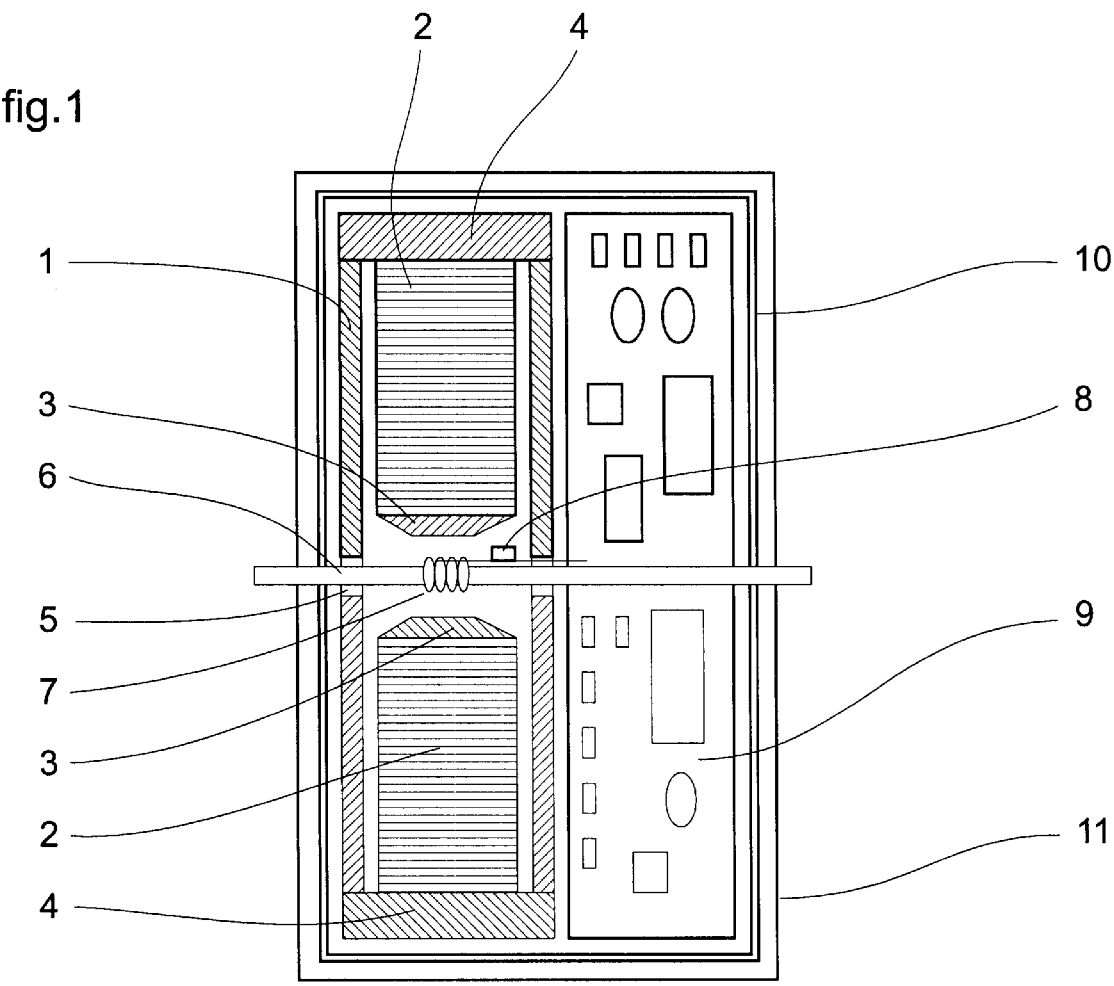
FIG. 1 is a schematic partially cross-sectional view of the implantable nuclear magnetic resonance spectrometer object of the present invention.

Referring to FIG. 1, there is shown one embodiment of a nuclear magnetic resonance spectrometer implantable device according to the invention. The static magnetic field is generated thanks to a permanent magnet arrangement. It is to be noted that the static magnetic field must comply with two criteria. Firstly the static magnetic field must be of high intensity. The intensity of the nuclear magnetic resonance signal is directly proportional to the number of atoms participating to the resonance, which is also directly proportional to the intensity of the magnetic field. Therefore, in order to generate a NMR signal that can be easily detected and analysed it is required to work with static magnetic field in the range of 1 Tesla and above. The second criterion that the magnetic field must fulfil is relative to its homogeneity. It is crucial that the sample to be analysed is immersed in whole in the same static magnetic field. If this is not the case, the de-excitation frequency spectrum will be broad ant thus difficult to measure and interpret. In the present case, the homogeneity of the static field should be in the range of 1–10 ppm.

A static magnetic field corresponding to these requirements is generated with an arrangement of permanent magnets. Back to FIG. 1, the arrangement of permanent magnets is constituted of a cylindrical external permanent magnet 1. The magnet arrangement comprises in addition two internal permanent magnets 2 also having a cylindrical shape. The magnets 1,2 are all polarised along their longitudinal axis. The direction of the magnetisation of both internal magnets 2 is identical but in the opposed direction of the polarisation of the external magnet 1. (i.e, if the north pole of the external magnet 1 is located at the upper part of the external magnet 1, the internal magnets 2 will have their north pole toward the bottom of the figure). The magnet arrangement is completed with two magneto-concentrator 3 located on adjacent poles of the internal magnets 2. Their function is to improve the intensity and the homogeneity of the static magnetic field in the region located directly in between the two internal magnets 2. Two ferrite caps 4 are closing this magnet arrangement and thus decreasing the loss of field appearing in that region.

The external magnet 1 is provided with two central radial holes 5 allowing the passage of a catheter 6 in between the two magneto-concentrators 3 ending the internal magnets 2. The fluid to analyse will flow in the catheter 6 in the center of the magnet arrangement. An excitation/detection coil 7 is arranged around the catheter 6 in the center of the permanent magnet structure. The volume of measure is determined by the volume of the coil which should be reduced in order to optimise the homogeneity of the field in the vicinity of the sample to analyse. Simulations have shown that homogeneity of 1 ppm is obtained with a sphere having a diameter of a 100 $\mu$m in the center of the structure for a field intensity of around 0,7 Tesla.

The excitation/detection coil 7 is connected to a electronic pre-preprocessing circuit 8 which, in a preferred embodiment, is located as close as possible to the coil 7 in order to increase the signal to noise ratio. This preprocessing circuit 8 which detects, amplify and pre-process the NMR signal is further connected to the main printed circuit board 9 which contains all the electronic components needed for the further processing of the signal. These known components will not be described in details in the present specification but their main function can be summarised as follow. The main printed circuit board 9 comprises the necessary components to generate the nuclear magnetic resonance excitation signal at the resonance frequency. It further comprises the required components to format the signal detected by the pre-processing circuit 8. The main circuit board 9 also includes the electronic components used for transferring the acquired and formatted data using state of the art telemetry. To that extent a RF antenna 10 is located in the housing 11 of the implantable device. When passive telemetry is used the antenna 10 serves both for energising the printed circuit boards by inductive coupling and for transferring the formatted measured data to an external reader. An example of passive absorption modulation telemetry is disclosed in detail in the granted European patent No EP 0377695B1.

In an alternative embodiment, a power source like a battery can be incorporated in the housing 11 of the implantable device. This is the case when the energy needed exceeds the energy that can be transmitted by telemetry. Active telemetry is widely used and known in the field of implantable medical devices. An apparatus and a method for telemetering both analog and digital data transcutaneously between an implantable medical device, like a pacemaker for example, and an external receiver or reader is described in U.S. Pat. No. 5,314,450 and can be implemented in order to transfer data bi-directionally between an external receiver (not shown) and the implantable device objet of the present invention.

The implantable device object of the invention will be encapsulated in a watertight housing in order to preserve the electronics components. The device may be for example completely encapsulated in a titanium housing which is bio-compatible and is therefore suitable for a long-term implantation in a human body. Watertight passages will be provided in the housing at the level of the catheter 6 so that the fluid to analyse may flow through the catheter 6 for example by diffusion.

Other isolation techniques may also be used, like the covering of the implantable device with bio-compatible polymers such as silicone or epoxy.

Thanks to the disclosed implantable device, it is possible to monitor continuously the composition and/or the concentration of specific chemical compounds in a physiological fluid. Once the device is implanted, it also allows the monitoring the fluid flow. One of the main advantage of this technique resides in the fact that it requires a one time implantation and then the implant can be interrogated non-invasively, by telemetry, whenever is needed and for as long time as needed. Many applications can be foreseen with this implantable device. By way of example, several use of the invention will be described.

Diabetic patients may need to test their blood glucose level several times a day. The proposed device objet of the invention may be implanted and then interrogated non-invasively by telemetry in order to perform an accurate monitoring of blood glucose level. This data will then be used to determine the optimal amount of insulin that needs to be injected. The implant could also be used to control automatically the injection rate of an implanted insulin infusion pump.

Other applications relates to the measurement of the effective flow rate out of an implanted drug delivery device as no implantable flow sensor are now available on the market. For example the knowledge of the effective flow rate in the shunt of a shunted hydrocephalic patient is a key for proper management of hydrocephalus. Implanting the proposed device along with the shunt would allow verifying that the shunt is working properly and allows optimisation of the settings of the shunt.

The implantable device may also be used for chronic monitoring of specific chemical compounds in a body fluid, in particular in trauma patients. Analytes that can be measured include metabolites such as amino acids, glucose, glutamate, lactose, dissolved gas, etc.

With such an implantable device, it is also possible to implement a feedback loop so that the implanted device may control other implantable devices like pacemaker or implanted drug delivery device depending on the results of the measured parameters.

What is claimed is:

1. An implantable nuclear magnetic resonance spectrometer for measuring the chemical composition of a fluid or for measuring the flow rate of the fluid, the spectrometer comprising:

a housing;

a catheter transversing across the housing so that a fluid external to the housing may flow through the catheter within the housing;

a permanent magnet disposed within the housing that generates an intense homogenous magnetic field in the vicinity of the catheter;

an electronics circuit disposed within the housing for detecting and formatting a nuclear magnetic resonance excitation signal; and at least one excitation coil connected to the electronic circuit and being disposed about the catheter to expose the fluid within the catheter to the excitation signal and to collect the nuclear magnetic resonance excitation signal.

2. An implantable nuclear magnetic resonance spectrometer according to claim 1, further comprising an antenna connected to the electric circuits for transmitting the formatted signal to an external reader unit by telemetry.

3. An implantable nuclear magnetic resonance spectrometer according to claim 1, wherein the permanent magnet comprises an external cylindrical magnet and two internal cylindrical permanent magnets, each of the magnets having a polarization along its axis of symmetry, the direction of the polarization of the external magnet being in the opposed direction of the polarization of the two internal cylindrical permanent magnets.

4. An implantable nuclear magnetic resonance spectrometer according to claim 3, wherein the permanent magnet further comprises two ferrite caps closing the external cylindrical magnet an two magneto concentrators located at the adjacent extremity of the two internal cylindrical permanent magnets.

5. An implantable nuclear magnetic resonance spectrometer according to claim 4, wherein the excitation coil is disposed around the catheter traversing the two cylindrical internal permanent magnets, and a pre-processing circuit being disposed adjacent to the at least one excitation coil, the pre-processing circuit detecting and pre-processing the nude magnetic resonance signal.

6. An implantable nuclear magnetic resonance spectrometer according to claim 1, further comprising a battery disposed within the housing for powering the electronic circuits.

7. An implantable nuclear magnetic resonance spectrometer according to claim 1, wherein the housing is encapsulated in a bio-compatible material.

8. An apparatus for measuring the chemical composition of a physiological fluid or for measuring the flow rate of the fluid, comprising:

an implantable nuclear magnetic resonance spectrometer having a catheter extending therethrough so that a fluid external to the spectrometer may flow through the catheter to be analyzed; and an external reader having means for communicating with the implantable spectrometer by telemetry.

9. A method of measuring the chemical composition of a physiological fluid and of measuring the flow rate of the fluid, the method comprising the steps of:

implanting in body passage a nuclear magnetic resonance spectrometer having:

a housing;

a catheter transversing across the housing so that a fluid external to the housing may flow through the catheter within the housing;

a permanent magnet disposed within the housing that generates an intense homogenous magnetic field in the vicinity of the catheter;

an electronic circuit disposed within the housing for detecting and formatting a nuclear magnetic resonance excitation signal; and at least one excitation coil connected to the electronic circuit and being disposed about the catheter to expose the fluid within the catheter to the excitation signal and to collect the nuclear magnetic resonance excitation signal;

energising and activating the implantable spectrometer with an external reader that is inductively coupled to the device; and collecting and analysing the data transmitted by the implantable spectrometer.

* * * * *

UNITED STATES PATENT AND TRADEMARK OFFICE
CERTIFICATE OF CORRECTION

PATENT NO.    : 6,600,945 B2
DATED         : July 29, 2003
INVENTOR(S)   : Ginggen et al.

It is certified that error appears in the above-identified patent and that said Letters Patent is hereby corrected as shown below:

Column 6,
Line 2, kindly delete "nude" and insert -- nuclear --.

Signed and Sealed this

Twenty-fifth Day of November, 2003

JAMES E. ROGAN
*Director of the United States Patent and Trademark Office*